US00PP11959P2

(12) United States Plant Patent
Li

(10) Patent No.: US PP11,959 P2
(45) Date of Patent: Jun. 26, 2001

(54) ***CAMPTOTHECA LOWREYANA* TREE NAMED 'KATIE'**

(75) Inventor: Shiyou Li, Nacogdoches, TX (US)

(73) Assignee: Stephen R. Austin State University, Nacogdoches, TX (US)

( * ) Notice: Subject to any disclaimer, the term of this patent is extended or adjusted under 35 U.S.C. 154(b) by 0 days.

(21) Appl. No.: 09/291,106

(22) Filed: Apr. 14, 1999

(51) Int. Cl.[7] ..... A01H 5/00
(52) U.S. Cl. ..... Plt./216

(58) Field of Search ..... Plt./216; 800/298

*Primary Examiner*—Bruce R. Campell
*Assistant Examiner*—Melissa L. Kimball
(74) *Attorney, Agent, or Firm*—C. A. Whealy

(57) ABSTRACT

A new and distinct cultivar of *Camptotheca lowreyana* tree named 'Katie', characterized by its freely and vigorously branching; dense and full plant habit; small leaf size; lanceolate to elliptic leaf shape; leaves from both juvenile and mature trees with entire leaf margins; lower temperature and drought tolerance; and high yield of anti-cancer camptothecin in leaves.

6 Drawing Sheets

BACKGROUND OF THE INVENTION

The present invention relates to a new and distinct cultivar of Camptotheca, botanically known as *Camptotheca lowreyana*, and hereinafter referred to by the name 'Katie'. The new Camptotheca is named in honor of Mrs. Katie Northrup of Houston, Tex.

Camptotheca, also known as Xi Shu or Happytrees, are deciduous trees, native to China, and a member of the Nyssaceae family. Three species of Camptotheca are significant sources of naturally-occurring camptothecins, a very promising anti-cancer chemical substance (Li et al., in press). The anti-tumor activity of Camptotheca was first discovered in 1957 (Wall et al., 1966). Clinical trials of camptothecins in the United States, China, Japan and Europe have shown success in treating may types of cancer (Li and Adair, 1994). Some camptothecin drugs have received approval for cancer treatment in more the 20 countries. Recently, three semi-synthetic drugs from camptothecins (Hycamtin, Campto, and 9-Nitrocamptothecin) were approved by the United State Food & Drug Administration for the treatment of ovarian, colorectal and pancreatic cancers. Camptothecins have also recently shown promise as inhibitors of HIV development in animal and human cell cultures (Priel, 1993).

Presently, production of camptothecins relies on Camptotheca trees. However, the production of Camptotheca trees is limited by low temperatures and drought. If new cultivars of Camptotheca that were more hardy and drought-tolerant were developed, the production of Camptotheca trees could be expanded.

The new Camptotheca is a product of a planned breeding program conducted by the Inventor in Nacogdoches, Tex. The objective of the breeding program is to create new Camptotheca cultivars that are more freely branching, have a higher camptothecin content and are tolerant to drought and low temperatues.

The new Camptotheca originated from a self-pollination made by the Inventor of the *Camptotheca lowreyana* Li (not patented). The cultivar Katie was discovered and selected by the Inventor within the progeny of the stated cross in a controllled environment in Nacogdoches, Tex., in April, 1995. The selection of this plant was based on its more freely branching habit, smaller leaf size, leaf shape, increased hardiness and tolerance to drought, and higher camptothecin content.

Asexual reproduction of the new Camptotheca by terminal cuttings harvested in a controlled environment in Nacogdoches, Tex., has shown that the unique features of this new Camptotheca are stable and reproduced true to type in successive generations.

BRIEF SUMMARY OF THE INVENTION

The new Camptotheca has not been observed under all possible environmental conditions. The phenotype may vary somewhat with variations in environment such as temperature, daylength, light intensity, nutrition and water status without, however, any variance in genotype.

The following traits have been repeatedly observed and are determined to be the unique characteristics of 'Katie'. These characteristics in combination distinguish 'Katie' as a new and distinct cultivar:

1. Freely and vigorously branching; dense and full plant habit.

2. Small leaf size.

3. Lanceolate to elliptic leaf shape.

4. Leaves from both juvenile and mature trees have entire margins.

5. Low temperature and drought tolerance.

6. High yield of anti-cancer camptothecin in leaves.

Plants of the new Camptotheca can be compared to plants of the parent cultivar *Camptotheca lowreyana* Li and *Camptotheca acuminata* Decaisne. However, in side-by-side comparisons conducted in Nacogdoches, Tex., plants of the new Camptotheca differ from plants of *Camptotheca lowreyana* Li and *Camptotheca acuminata* Decaisne in the following charcteristics:

1. Plants of the new Camptotheca are more freely branching and denser and fuller than plants of *Camptotheca lowreyana* Li and *Camptotheca acuminata* Decaisne.

2. Leaves of plants of the new Camptotheca are much smaller than leaves of plants of *Camptotheca lowreyana* Li and *Camptotheca acuminata* Decaisne.

3. Leaves of plants of the new Camptotheca are different in shape compared to plants of *Camptotheca lowreyana* Li and *Camptotheca acuminata* Decaisne.

4. Leaves from juvenile plants of the new Camptotheca have entire margins whereas leaves from juvenile plants of *Camptotheca lowreyana* Li and *Camptotheca acuminata* Decaisne have serrated margins.

5. Plants of the new Camptotheca are more tolerant to low temperatures and drought than plants of *Camptotheca lowreyana* Li and *Camptotheca acuminata* Decaisne.

6. Plants of the new Camptotheca have a higher yield of camptothecin than plants of *Camptotheca lowreyana* Li and *Camptotheca acuminata* Decaisne.

A comparison of one-year old plants of the new Camptotheca, *Camptotheca lowreyana* Li, and *Camptotheca acuminata* Decaisne appears in Chart A at the end of the specification.

BRIEF DESCRIPTION OF THE DRAWINGS

The accompanying colored photographs illustrate the overall appearance of the new Camptotheca, showing the colors as true as it is reasonably possible to obtain in colored reproductions of this type. Colors in the photographs may differ slightly from the color values cited in the detailed botanical description which more accurately describe the actual colors of the new Camptotheca.

FIG. 1 comprises a side perspective view of a typical plant of 'Katie' showing the freely and vigorously branching habit.

FIG. 2 comprises a close-up view of leaves and lateral branches of a typical plant of 'Katie'.

FIG. 3 comprises a top perspective view of typical plants of *Camptotheca acuminata* Decaisne (left) and 'Katie' (right) showing the differences in growth habit and leaf size.

FIG. 4 comprises a close-up view of typical leaves (upper and lower surfaces) from two-year old plants of *Camptotheca lowreyana* Li (A); the cultivar 'Katie' (B); *Camptotheca yunnanensis* Dode (C); and *Camptotheca acuminata* Decaisne (D).

DETAILED BOTANICAL DESCRIPTION

Figure 5:
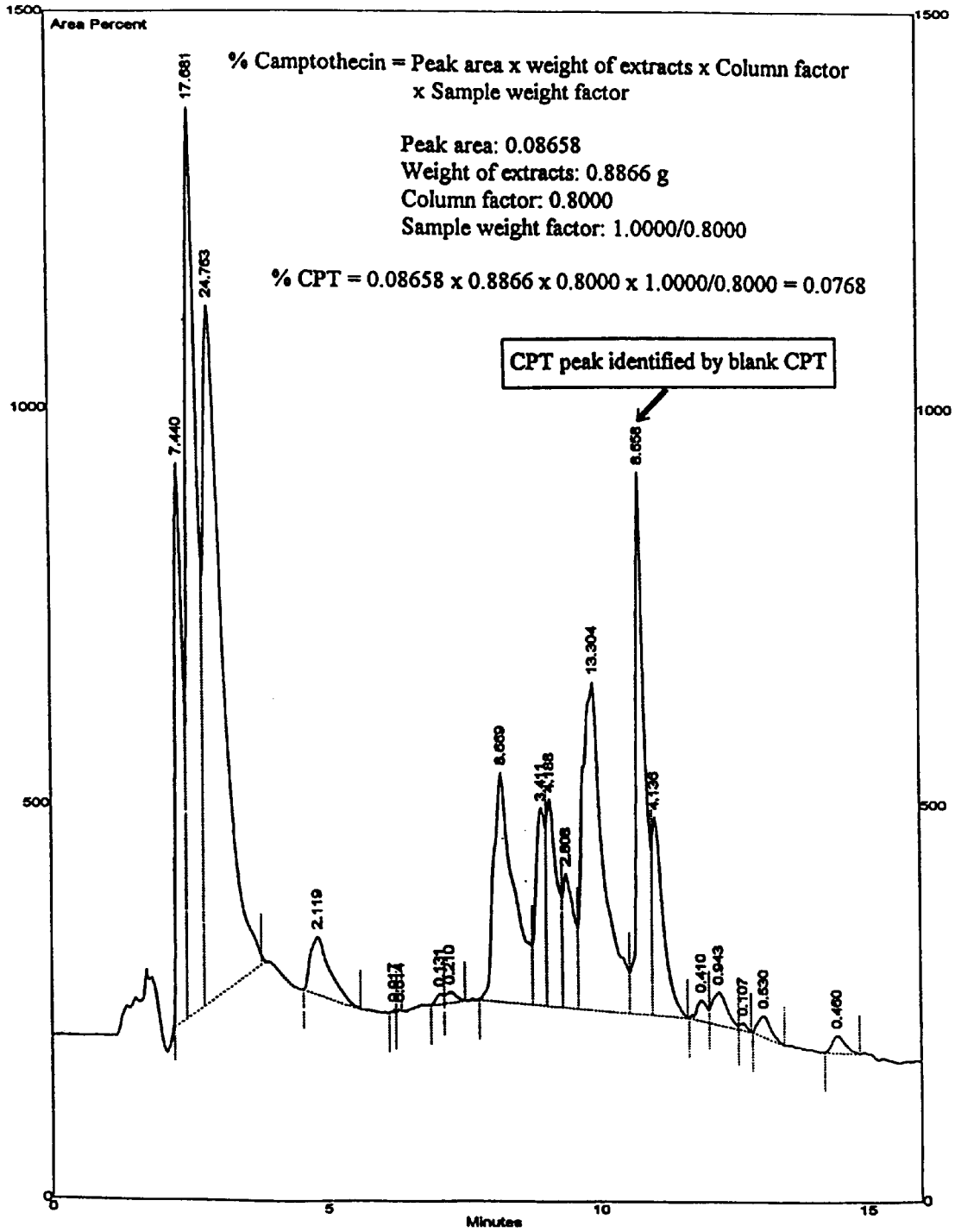
FIG. 5 of illustrations comprises camptothecin concentrations of young leaves of the new Camptotheca as determined by high performance liquid chromatography (HPLC).
Figure 6:
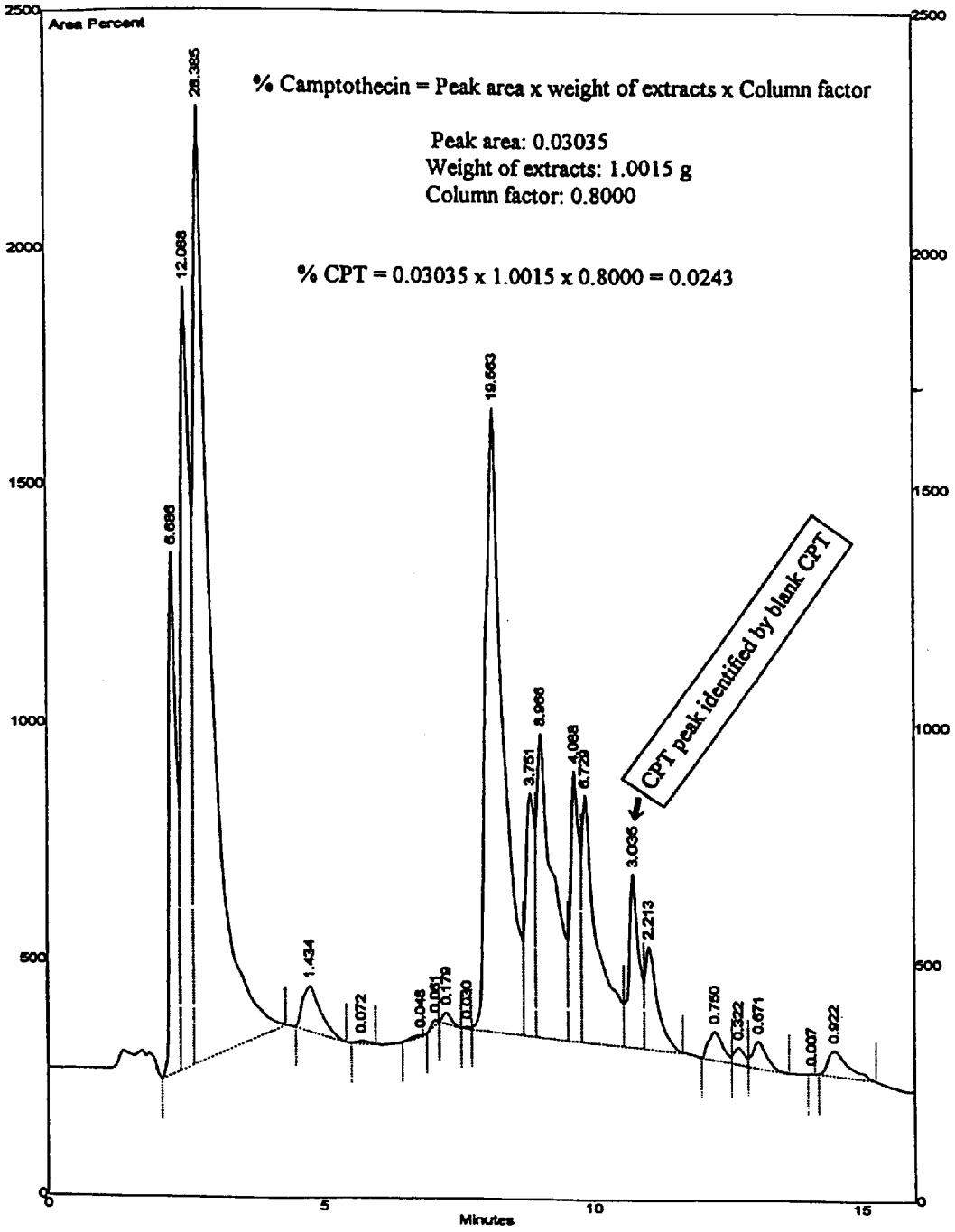
FIG. 6 of illustrations comprises camptothecin concentrations of mature leaves of the new Camptotheca as determined by high performance liquid chromatography (HPLC).

The aforementioned and following observations, measurements, values, and comparisons described plants grown in Nacogdoches, Tex., in one-gallon containers under outdoor conditions which closely approximate commercial production conditions. Plants used for the description were approximately one-year old.

In the following description, color references are made to The Royal Horticultural Society Colour Chart except where general terms of ordinary dictionary significance are used.

Botanical classification: *Camptotheca lowreyana* 'Katie'.

Parentage:

*Male parent.*—*Camptotheca lowreyana* Li, not patented.

*Female parent.*—*Camptotheca lowreyana* Li, not patented.

Propagation:

*Type.*—By terminal cuttings.

*Time to initiate roots.*—Summer: About 7 days at temperatures of 32° C. Winter: About 15 days at temperatures of 21° C.

*Time to develop roots.*—Summer: About 21 days at temperatures of 32° C. Winter: About 40 days at temperatures of 21° C.

*Rooting habit.*—Fibrous.

Plant description:

*Plant type.*—Polygamous, deciduous tree with medicinal and ornamental value.

*Growth habit.*—Conical; compact; dense and full.

*Branching habit.*—Very freely and vigorously branching with about 10 to 35 lateral branches developing in the first year of growth.

*Plant height, soil level to top of leaves.*—About 1.5 to 2 meters; plants attain a plant height of about 15 meters at maturity.

*Plant diameter, area of spread.*—About 0.5 meters; plants may attain a plant diameter of about 10 meters at maturity.

*Growth rate.*—Rapid, vigorous.

*Lateral branch length.*—About 5 to 20 cm.

*Stem color.*—Immature stems, 2 weeks old, 59B; from 2 weeks to 6 months old, 146A; from 6 months to 2 years, 152A; older than 2 years, 148A.

*Stem texture.*—Young bark, less than 5 years old, smooth with scattered lenticels, 159A in color.

*Stem pubescence.*—Dense.

Foliage descripton:

*Arrangement.*—Alternate, single, numerous.

*Length.*—About 4 to 10 cm.

*Width.*—About 1.5 to 4 cm.

*Shape.*—Lanceolate to elliptic.

*Apex.*—Acute or acuminate.

*Base.*—Cuneate or oblique.

*Margin, juvenile and mature plants.*—Entire; slightly undulating with glands.

*Texture.*—Upper surface: Smooth, slightly glabrous, slightly lustrous. Lower surface: Glabrous and lusterless; moderately pubescent.

*Venation pattern.*—Pinnate, 10 to 15 lateral viens per leaf.

*Stomates.*—Frequency: About 211 per $\mu m^2$. Length: About 29 $\mu m$.

*Gland length.*—About 42 $\mu m$.

*Color.*—Young foliage, upper surface: Initially 59A under full sun conditions, then becoming close to 143A or 143B. Young foliage, lower surface: Initially 60B under full sun conditions, then becoming close to 144A. Mature foliage, upper surface: Close to 137A. Mature foliage, lower surface: Close to 146B or 137C. Venation, upper surface: Close to 145A or 145B. Venation, lower surface: Close to 145B or 145C.

*Petiole.*—Length: About 5 to 10 mm. Diameter: About 1 to 1.5 mm. Color: Initially 45B to 59A under full sun conditions, then becoming close to 146C.

Flower description:

*Natural flowering season.*—May through August in the Northern Hemisphere, flowering continuous. Flowers persistent.

*Flower arrangement.*—Very small cyanthiform single flowers. Two sessile flowers are arranged as a cyme with 15 to 30 cymes forming a dense spherical inflorescence. Two to ten inflorescences are arranged as a terminal or axillary raceme or panicle-like compound inflorescence. Flowers on the upper part of the compound inflorescence are bisexual and flower first; the lower flowers are male or sometimes bisexual.

*Time to flower.*—Trees are usually about 4 to 6-years old before flowering commences; thereafter, prolific flowering is typical.

*Quantity of flowers.*—Flowering trees may develop up to 1500 flowers per lateral stem.

*Time of flower opening.*—About 5 to 20 days.

*Fragrance.*—Strong, but pleasant.

*Inflorescence length.*—About 1.5 to 2 cm.

*Inflorescence width.*—About 1.5 to 2 cm.

*Flower diameter.*—About 3 to 8 mm.

*Flower height.*—About 7 to 15 mm.

*Flower longevity on plant.*—About 20 to 45 days depending on temperature and precipitation.

*Flower bud.*—Length: About 4 to 10 mm. Diameter: About 2 to 5 mm. Shape: Ovoid.

*Petals.*—Appearance: Glossy. Quantity: Five per flower. Texture: Pubescent. Arrangement: Imbricate. Shape: Oblong to ovate with acute apex. Margin: Entire. Length: About 1.2 to 1.5 cm. Width: About 0.4 to 0.8 mm. Color: When opening, upper and lower surfaces: Light green, close to 138C. Fully opened, upper and lower surfaces: Yellowish green, close to 145C.

*Sepals.*—Appearance: Glossy. Quantity: Five per flower. Texture: Ciliate. Arrangement: Fused as cyanthiform calyx. Shape: Deltoid with acute apex. Margin: Entire. Calyx length: About 4 to 10 mm Calyx diameter: About 2 to 4 mm. Color, upper and lower surfaces: Light green, close to 138B.

*Peduncles.*—Length: About 2 to 8 mm. Angle: Erect. Strength: Strong. Color: Light gray, close to 191B.

*Reproductive organs.*—Androecium: Stamen number: Usually ten. Anther shape: Four-locular. Anther size: About 0.5 mm by 1 mm. Anther color: Bright yellow. Amount of pollen: Moderate. Pollen color: Yellow. Gynoecium: Pistil length: About 5 to 10 mm. Stigma shape: 2 to 3-lobed. Stigma color: Yellowish green. Style length: About 2 to 7 mm.

*Seed.*—Fruit type: Samara-like. Length: About 2.7 cm. Diameter: About 5 mm. Color: 164B or 164C.

Disease resistance: Resistance to diseases common to Camptotheca is similar to other Camptothecas grown under typical commercial conditions.

Hardiness: The new Camptotheca is hardy to USDA zone 8 with −10° C. the apparent critical low temperature. In field trials in Nacogdoches, Tex., the new Camptotheca did not exhibit frost damage when exposed to −14° C. in February, 1997, whereas other varieties of Camptotheca exhibited damage.

Drought tolerance: According to the field trials in summer of 1996, the new Camptotheca was the most drought-tolerant of all Camptotheca varieties tested.

CHART A

| CHARACTER | *Camptotheca lowreyana* 'Katie' | *Camptotheca lowreyana* Li | *Camptotheca acuminata* Decaisne |
|---|---|---|---|
| NUMBER OF LATERAL BRANCHES | About 10 to 35 | Fewer than 5 | Fewer than 5 |
| LEAF LENGTH | About 4 to 10 cm | About 12 to 25 cm | About 14 to 20 cm |
| LEAF WIDTH | About 1.5 to 4 cm | About 7 to 10 cm | About 7 to 10 cm |
| LEAF SHAPE | Lanceolate/elliptic | Cordate/ovate | Oval/oblong |
| LEAF BASE | Cuneate/oblique | Cordate/rounded | Equilateral/cuneate |
| LEAF MARGIN, JUVENILE PLANTS | Entire | Serrate | Serrate |
| LEAF MARGIN, MATURE PLANTS | Entire | Entire | Entire |
| LEAF LUSTER, LOWER SURFACE | Lusterless | Lustrous | Lusterless |
| PETIOLE LENGTH | About 5 to 10 mm | About 1.5 to 3 cm | About 1.5 to 3 cm |
| PETIOLE DIAMETER | About 1 to 1.5 mm | About 2.5 to 4.5 mm | About 2.5 to 5 mm |
| HARDINESS | To zone 8 | To zone 9 | To zone 9 |
| CAMPTOTHECIN YIELD, YOUNG LEAVES | 0.077% | 0.055% | 0.042% |
| CAMPTOTHECIN YIELD, MATURE LEAVES | 0.024% | 0.013% | 0.019% |

LIST OF REFERENCES

Li, S.Y., *Camptotheca lowreyana*, a new species of anti-cancer happytrees (Camptotheca Decaisne). *Bull. Bot. Res.* 17(3): 348–352 (1997).

Li, S.Y. and K.T. Adair, *Camptotheca acuminata* Decaisne, Xi Shu, *A Promising Anti-Tumor and Anti-Viral Tree for the 21st Century*. Nacogdoches, Tex.: College of Forestry, Stephen F. Austin State University (1994).

Li, S.Y. et al., *Anti-Cancer Happytrees*. Nacogdoches, Tex.: Arthur Temple College of Forestry, Stephen F. Austin State University (in press).

Priel, E. et al., Inhibition of retrovirus-induced disease in mice by camptothecin. *Jour. of Virology* 67(6):3624–3629 (1993).

Wall, M.E. et al., *J. Am. Chem. Soc.* 88:3888–3890 (1966).

It is claimed:

1. A new and distinct *Camptotheca lowreyana* tree named 'Katie', as illustrated and described.

* * * * *